United States Patent
Shatunov et al.

(10) Patent No.: US 9,748,606 B2
(45) Date of Patent: Aug. 29, 2017

(54) ADDITIVE FOR ELECTROLYTE OF LITHIUM BATTERY, ELECTROLYTE INCLUDING THE SAME, AND LITHIUM BATTERY USING THE ELECTROLYTE

(71) Applicant: SAMSUNG SDI CO., LTD., Yongin-si, Gyeonggi-do (KR)

(72) Inventors: Pavel Alexandrovich Shatunov, Yongin-si (KR); Sanghoon Kim, Yongin-si (KR); Harim Lee, Yongin-si (KR); Makhmut Khasanov, Yongin-si (KR); Inhaeng Cho, Yongin-si (KR); Woocheol Shin, Yongin-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 134 days.

(21) Appl. No.: 14/705,306

(22) Filed: May 6, 2015

(65) Prior Publication Data
US 2016/0056503 A1    Feb. 25, 2016

(30) Foreign Application Priority Data
Aug. 25, 2014 (KR) .................. 10-2014-0111046

(51) Int. Cl.
  *H01M 10/052*  (2010.01)
  *H01M 10/0567* (2010.01)
  *C07F 9/6521*  (2006.01)
  *H01M 10/0569* (2010.01)
  *H01M 10/0568* (2010.01)

(52) U.S. Cl.
  CPC ..... *H01M 10/0567* (2013.01); *C07F 9/65216* (2013.01); *H01M 10/052* (2013.01); *H01M 10/0568* (2013.01); *H01M 10/0569* (2013.01); *H01M 2220/30* (2013.01); *H01M 2300/0037* (2013.01)

(58) Field of Classification Search
  CPC ................ H01M 10/052; H01M 10/0567
  See application file for complete search history.

(56) References Cited

U.S. PATENT DOCUMENTS

| | | | | |
|---|---|---|---|---|
| 2,685,581 A | * | 8/1954 | Coover, Jr. | C07F 9/65216 106/170.1 |
| 5,534,573 A | * | 7/1996 | Leake | C07F 9/65216 523/451 |
| 6,630,272 B1 | * | 10/2003 | Iwamoto | H01M 6/168 429/328 |
| 2009/0053599 A1 | | 2/2009 | Ichihashi et al. | |
| 2012/0045697 A1 | | 2/2012 | Park et al. | |
| 2012/0315536 A1 | | 12/2012 | Bhat et al. | |
| 2013/0004859 A1 | | 1/2013 | Yu et al. | |

FOREIGN PATENT DOCUMENTS

| | | |
|---|---|---|
| KR | 10-0704104 | 3/2007 |
| KR | 10-1125653 | 3/2012 |
| KR | 10-2013-0003865 | 1/2013 |
| KR | 10-1318522 | 10/2013 |

* cited by examiner

Primary Examiner — Olatunji Godo
(74) Attorney, Agent, or Firm — Lee & Morse, P.C.

(57) ABSTRACT

Provided are an additive for an electrolyte of a lithium battery; an electrolyte having the same; and a lithium battery using the electrolyte. The additive for an electrolyte of a lithium battery includes a triazine triphosphonate compound.

16 Claims, 3 Drawing Sheets

ADDITIVE FOR ELECTROLYTE OF LITHIUM BATTERY, ELECTROLYTE INCLUDING THE SAME, AND LITHIUM BATTERY USING THE ELECTROLYTE

CROSS-REFERENCE TO RELATED APPLICATION

Korean Patent Application No. 10-2014-0111046, filed on Aug. 25, 2014, in the Korean Intellectual Property Office, and entitled: "Additive for Electrolyte of Lithium Battery, Electrolyte Including the Same, and Lithium Battery Using the Electrolyte," is incorporated by reference herein in its entirety.

BACKGROUND

1. Field

Embodiments relate to an additive for an electrolyte of a lithium battery, an electrolyte of the lithium battery including the same, and a lithium battery using the electrolyte.

2. Description of the Related Art

A lithium battery is widely used as a power source for portable electronic devices such as a video camera, a cell phone, and a notebook. A rechargeable lithium battery (secondary battery) has a large energy density per unit weight, which is three times greater than that of batteries such as a lead storage battery, a nickel-cadmium battery, a nickel hydrogen battery, and a nickel zinc battery, and may be charged rapidly.

SUMMARY

Embodiments are directed to an additive for an electrolyte of a lithium battery, the additive including a triazine triphosphonate compound.

The triazine triphosphonate compound may be a 1,3,5-triazine-2,4,6-triphosphonate compound.

The triazine triphosphonate compound may be represented by Formula 1 below:

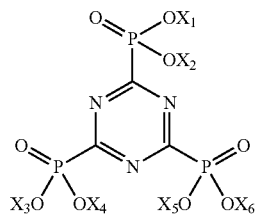

[Formula 1]

In Formula 1, $X_1$, $X_2$, $X_3$, $X_4$, $X_5$, and $X_6$ may each independently be hydrogen, a halogen atom, a substituted or unsubstituted $C_1$-$C_{30}$ alkyl group, a substituted or unsubstituted $C_1$-$C_{30}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_7$-$C_{20}$ arylalkyl group, a substituted or unsubstituted $C_2$-$C_{20}$ heteroaryl group, a substituted or unsubstituted $C_2$-$C_{20}$ heteroaryloxy group, a substituted or unsubstituted $C_2$-$C_{20}$ heteroarylalkyl group, a substituted or unsubstituted $C_4$-$C_{20}$ cyclic group, a substituted or unsubstituted $C_4$-$C_{20}$ cyclic alkyl group, a substituted or unsubstituted $C_2$-$C_{20}$ heterocyclic group, a substituted or unsubstituted $C_2$-$C_{20}$ heterocyclic alkyl group, a cyano group, an amino group, an amidino group, a hydrazine group, a hydrazone group, a nitro group, a phosphonate group, a silyl group, a carboxyl group or a salt thereof, a sulfonyl group, a sulfamoyl group, a sulfonic acid group or a salt thereof, or a phosphoric acid group or a salt thereof.

The triazine triphosphonate compound may be a silylated triazine triphosphonate compound.

The triazine triphosphonate compound may be a silylated 1,3,5-triazine-2,4,6-triphosphonate compound.

The triazine triphosphonate compound may be represented by Formula 2 below:

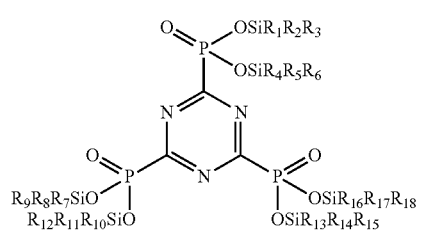

[Formula 2]

In Formula 2, $R_1$ to $R_{18}$ may each independently be hydrogen, a halogen atom, a substituted or unsubstituted $C_1$-$C_{30}$ alkyl group, a substituted or unsubstituted $C_1$-$C_{30}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_7$-$C_{20}$ arylalkyl group, a substituted or unsubstituted $C_2$-$C_{20}$ heteroaryl group, a substituted or unsubstituted $C_2$-$C_{20}$ heteroaryloxy group, a substituted or unsubstituted $C_2$-$C_{20}$ heteroarylalkyl group, a substituted or unsubstituted $C_4$-$C_{20}$ cyclic group, a substituted or unsubstituted $C_4$-$C_{20}$ cyclic alkyl group, a substituted or unsubstituted $C_2$-$C_{20}$ heterocyclic group, a substituted or unsubstituted $C_2$-$C_{20}$ heterocyclic alkyl group, a cyano group, a hydroxyl group, an amino group, an amidino group, a hydrazine group, a hydrazone group, a nitro group, a thiol group, a carboxyl group or a salt thereof, a sulfonyl group, a sulfamoyl group, a sulfonic acid group or a salt thereof or a phosphoric acid group or a salt thereof.

In Formula 2, $R_1$ to $R_{18}$ may each independently be substituted or unsubstituted $C_1$-$C_{30}$ alkyl groups.

In Formula 2, $R_1$ to $R_{18}$ may each independently be a methyl group, an ethyl group, a propyl group, an isopropyl group, a butyl group, a tert-butyl group, a trifluoromethyl group, or a tetrafluoroethyl group.

The triazine triphosphonate compound may be represented by Formula 3 below:

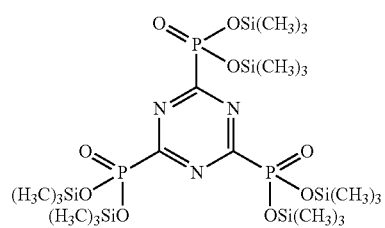

[Formula 3]

Embodiments are also directed to a lithium battery electrolyte, including a non-aqueous organic solvent, a lithium salt, and the additive according to an embodiment.

The amount of the additive may be in a range of about 0.001 wt % to about 10 wt % based on the total weight of the electrolyte.

The amount of the additive may be in a range of about 0.01 wt % to about 5 wt % based on the total weight of the electrolyte.

The non-aqueous organic solvent may include one or more of a carbonate-based solvent, an ester-based solvent, an ether-based solvent, a ketone-based solvent, an alcohol-based solvent, or an aprotic solvent.

The non-aqueous organic solvent may include one or more of dimethyl carbonate (DMC), diethyl carbonate (DEC), dipropyl carbonate (DPC), methyl propyl carbonate (MPC), ethyl propyl carbonate (EPC), methyl ethyl carbonate (MEC), ethylene carbonate (EC), propylene carbonate (PC), butylene carbonate (BC), fluoroethylene carbonate (FEC), vinylene carbonate (VC), acetonitrile, succinonitrile (SN), dimethyl sulfoxide, dimethyl formamide, dimethyl acetamide, γ-butyrolactone, tetrahydrofuran, or ethyl propionate (EP).

The lithium salt may include one or more of $LiPF_6$, $LiBF_4$, $LiSbF_6$, $LiAsF_6$, $LiC4F_9SO_3$, $LiClO_4$, $LiAlO_2$, $LiAlCl_4$, $LiN(C_xF_{2x+1}SO_2)(C_yF_{2y+1}SO_2)$ where x and y are each independently an integer of 1 to 10, LiCl, LiI, $LiB(C_2O_4)_2$ (lithium bis(oxalato)borate), or a combination thereof.

The concentration of the lithium salt may be in a range of about 0.1 M to about 2.0 M.

Embodiments are also directed to a lithium battery, including a positive electrode, a negative electrode, and the electrolyte according to an embodiment.

BRIEF DESCRIPTION OF THE DRAWINGS

Features will become apparent to those of ordinary skill in the art by describing in detail example embodiments with reference to the attached drawings in which.

DETAILED DESCRIPTION

Figure 1:
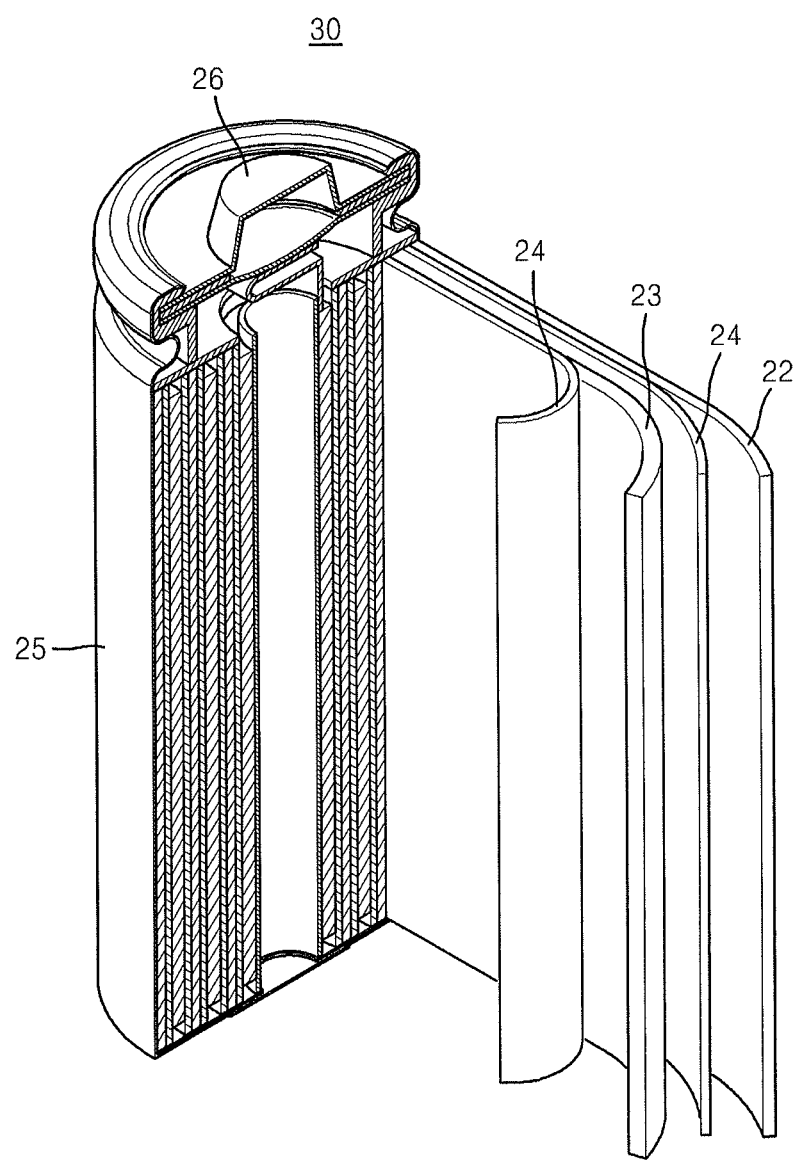
FIG. 1 is a schematic view of a lithium battery according to an Example of the present invention.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

As used herein, the term "and/or" includes any and all combinations of one or more of the associated listed items. Expressions such as "at least one of" when preceding a list of elements, modify the entire list of elements and do not modify the individual elements of the list.

According to an example embodiment, an additive for an electrolyte of a lithium battery includes a triazine triphosphonate compound. Here, the term "a triazine triphosphonate compound" refers to a compound with a triazine backbone structure having three phosphonate groups.

According to an example embodiment, the triazine triphosphonate compound may be a 1,3,5-triazine-2,4,6-triphosphonate compound.

According to an example embodiment, the triazine triphosphonate compound may be represented by Formula 1 below,

[Formula 1]

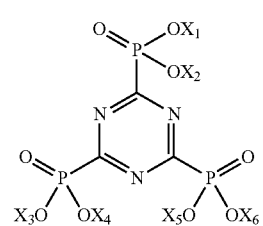

According to the present example embodiment, in Formula 1, $X_1$, $X_2$, $X_3$, $X_4$, $X_5$, and $X_6$ are each independently hydrogen, a halogen atom, a substituted or unsubstituted $C_1$-$C_{30}$ alkyl group, a substituted or unsubstituted $C_1$-$C_{30}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_7$-$C_{20}$ arylalkyl group, a substituted or unsubstituted $C_2$-$C_{20}$ heteroaryl group, a substituted or unsubstituted $C_2$-$C_{20}$ heteroaryloxy group, a substituted or unsubstituted $C_2$-$C_{20}$ heteroarylalkyl group, a substituted or unsubstituted $C_4$-$C_{20}$ cyclic group, a substituted or unsubstituted $C_4$-$C_{20}$ cyclic alkyl group, a substituted or unsubstituted $C_2$-$C_{20}$ heterocyclic group, a substituted or unsubstituted $C_2$-$C_{20}$ heterocyclic alkyl group, a cyano group, an amino group, an amidino group, a hydrazine group, a hydrazone group, a nitro group, a phosphonate group, a silyl group, a carboxyl group or a salt thereof, a sulfonyl group, a sulfamoyl group, a sulfonic acid group or a salt thereof, a phosphoric acid group or a salt thereof.

According to an example embodiment, the triazine triphosphonate compound may be a silylated triazine triphosphonate compound.

According to an example embodiment, the triazine triphosphonate compound may be represented by Formula 2 below,

[Formula 2]

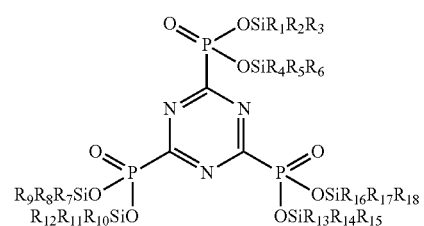

According to the present example embodiment, in Formula 2, $R_1$ to $R_{18}$ are each independently hydrogen, a halogen atom, a substituted or unsubstituted $C_1$-$C_{30}$ alkyl group, a substituted or unsubstituted $C_1$-$C_{30}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_7$-$C_{20}$ arylalkyl group, a substituted or unsubstituted $C_2$-$C_{20}$ heteroaryl group, a substituted or unsubstituted $C_2$-$C_{20}$ heteroaryloxy group, a substituted or unsubstituted $C_2$-$C_{20}$ heteroarylalkyl group, a substituted or unsubstituted $C_4$-$C_{20}$ cyclic group, a substituted or unsubstituted $C_4$-$C_{20}$ cyclic alkyl group, a substituted or unsubstituted $C_2$-$C_{20}$ heterocyclic group, a substituted or unsubstituted $C_2$-$C_{20}$ heterocyclic alkyl group, a cyano group, a hydroxyl group, an amino group, an amidino group, a hydrazine group, a hydrazone group, a nitro group, a thiol group, a carboxyl group of a salt thereof, a sulfonyl group, sulfamoyl group, a sulfonic acid group or a salt thereof, or a phosphoric acid group or a salt thereof.

According to an example embodiment, in Formula 2, $R_1$ to $R_{18}$ may be a substituted or unsubstituted $C_1$-$C_{30}$ alkyl group. For example, in Formula 2, $R_1$ to $R_{18}$ may each independently be a methyl group, an ethyl group, a propyl group, an isopropyl group, a butyl group, a tert-butyl group, a trifluoromethyl group, or a tetrafluoroethyl group.

According to an example embodiment, the triazine triphosphonate compound may be a compound represented by Formula 3 below.

[Formula 3]

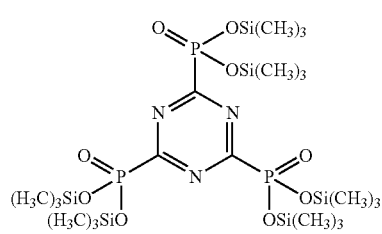

Hereinafter are definitions of functional groups and substituents used in the chemical formulae herein.

The term "alkyl" used in a chemical formula refers to a fully saturated branched or unbranched (or straight chain or linear) hydrocarbon.

Examples of the "alkyl" include methyl, ethyl, n-propyl, isopropyl, n-butyl, isobutyl, sec-butyl, n-pentyl, isopentyl, neopentyl, iso-amyl, n-hexyl, 3-methylhexyl, 2,2-dimethylpentyl, 2,3-dimethyl pentyl, n-heptyl, etc.

At least one hydrogen atom in the "alkyl" may be substituted. Substituents, which may replace the at least one hydrogen, include a halogen atom, a $C_1$-$C_{20}$ alkyl group (e.g., $CCF_3$, $CHCF_2$, $CH_2F$, or $CCl_3$) substituted with a halogen atom, a $C_1$-$C_{20}$ alkoxy group, a $C_2$-$C_{20}$ alkoxyalkyl group, a hydroxyl group, a nitro group, a cyano group, an amino group, an amidino group, a hydrazine group, a hydrazone group, a carboxylic acid or a salt thereof, a sulfonyl group, a sulfamoyl group, a sulfonic acid or a salt thereof, phosphoric acid or a salt thereof, or a $C_1$-$C_{20}$ alkyl group, a $C_2$-$C_{20}$ alkenyl group, a $C_2$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, a $C_7$-$C_{20}$ heteroarylalkyl group, a $C_6$-$C_{20}$ heteroaryloxy group, a $C_6$-$C_{20}$ heteroaryloxyalkyl group, and a $C_6$-$C_{20}$ heteroarylalkyl group.

The term "halogen atom" includes fluorine, bromine, chlorine, and iodine atoms.

The term "$C_1$-$C_{20}$ alkyl group substituted with a halogen atom" refers to a $C_1$-$C_{20}$ alkyl group that is substituted with at least one halo group, and examples of the "$C_1$-$C_{20}$ alkyl group substituted with a halogen atom" include monohaloalkyl or polyhaloalkyl including dihaloalkyl or perhaloalkyl.

The monohaloalkyl includes one iodine, bromine, chlorine, or fluorine in the alkyl group, and dihaloalkyl or polyhaloalkyl refers to an alkyl group having at least two halogen atoms that are identical to or different from each other.

The term "alkoxy" used in a chemical formula refers to alkyl-O—, and the alkyl group is as described above. Examples of the alkoxy include methoxy, ethoxy, propoxy, butoxy, tert-butoxy, pentyloxy, hexyloxy, cyclopropoxy, and cyclohexyloxy. In the alkoxy group, at least one hydrogen atom may be substituted with the same substituent groups as described above in connection with the alkyl group.

The term "alkoxyalkyl" used in a chemical formula refers to the case when an alkyl group is substituted with the alkoxy group described above. At least one hydrogen atom of the alkoxyalkyl may be substituted with the same substituent groups as described above in connection with the alkyl group. The term "alkoxyalkyl" includes an alkoxyalkyl moiety.

The term "alkenyl" used in a chemical formula refers to a branched or non-branched hydrocarbon having at least one carbon-carbon double bond. Examples of the alkenyl group include vinyl, allyl, butenyl, isopropenyl, and isobutenyl, and at least one hydrogen atom of the alkenyl group may be substituted with the same substituent groups as described above in connection with the alkyl group.

The term "alkynyl" used in a chemical formula refers to a branched or non-branched hydrocarbon having at least one carbon-carbon triple bond. Examples of the alkynyl group include ethynyl, butyryl, isobutynyl, and isopropynyl.

At least one hydrogen atom of the alkynyl group may be substituted with the same substituent groups as described above in connection with the alkyl group.

The term "aryl" used in a chemical formula refers to an aromatic hydrocarbon that may be used alone or in a combination and includes at least one ring.

The term "aryl" includes a group wherein aromatic rings are fused together and/or with one or more cycloalkyl rings.

Examples of the aryl include phenyl, naphthyl, and tetrahydronaphthyl.

Also, at least one hydrogen atom in the aryl group may be substituted with the same substituent groups as described above in connection with the alkyl group.

The term "arylalkyl" used in a chemical formula refers to an alkyl group substituted with an aryl group. Examples of the arylakyl include benzyl and phenyl-$CH_2CH_2$—.

The term "aryloxy" used in a chemical formula refers to —O-aryl, and examples of the aryloxy group include phenoxy. At least one hydrogen atom in the aryl group may be substituted with the same substituent groups as described above in connection with the alkyl group.

The term "heteroaryl" used in a chemical formula refers to a monocyclic or bicyclic organic compound including at least one heteroatom selected from N, O, P, and S, and the remaining ring atoms are C. For example, the heteroaryl group may include 1 to 5 heteroatoms and may include 5 to 10 ring members, wherein S or N may be oxidized to various oxidation states.

At least one hydrogen atom in the heteroaryl group may be substituted with the same substituent groups as described above in connection with the alkyl group.

The term "heteroarylalkyl" refers to an alkyl group substituted with heteroaryl.

The term "heteroaryloxy" refers to a —O-heteroaryl moiety. At least one hydrogen atom in the heteroaryloxy group may be substituted with the same substituent groups as described above in connection with the alkyl group.

The term "heteroaryloxyalkyl" refers to an alkyl group substituted with —O— heteroaryl. At least one hydrogen atom in the heteroaryloxyalkyl group may be substituted with the same substituent groups as described above in connection with the alkyl group.

The term "cyclic group" used in a chemical formula refers to a saturated or partially unsaturated non-aromatic monocyclic, bicyclic, or tricyclic hydrocarbon group.

Examples of the cyclic group include cyclopentyl, cyclopentenyl, cyclohexyl, cyclohexenyl, and adamantyl.

At least one hydrogen atom in the "cyclic group" may be substituted with the same substituent groups as described above in connection with the alkyl group.

The term "heterocyclic group" used in a chemical formula refers to a cyclic group composed of 5 to 10 atoms containing a heteroatom, such as nitrogen, sulfur, phosphor, or oxygen. In particular, an example of the hetero-ring group is pyridyl, and at least one hydrogen atom in the "hetero-ring group" may be substituted with the same substituent groups as described above in connection with the alkyl group.

The term "heterocyclic oxy" refers to an —O-heterocyclic (—O-hetero ring), and at least one hydrogen atom in the "heterocyclic oxy" group may be substituted with the same substituent groups as described above in connection with the alkyl group.

The term "sulfonyl" refers to R"—SO$_2$—, wherein. R" is a hydrogen atom, alkyl, aryl, heteroaryl, aryl-alkyl, heteroaryl-alkyl, alkoxy, aryloxy, cycloalkyl group, or a heterocyclic group.

The term "sulfamoyl" refers to H$_2$NS(O$_2$)—, alkyl-NHS(O$_2$)—, (alkyl)$_2$NS(O$_2$)-aryl-NHS(O$_2$)—, alkyl(aryl)-NS(O$_2$)—, (aryl)$_2$NS(O)$_2$, heteroaryl-NHS(O$_2$)—, (aryl-alkyl)-NHS(O$_2$)—, or (heteroaryl-alkyl)-NHS(O$_2$)—.

At least one hydrogen atom in the "sulfamoyl group" may be substituted with the same substituent groups as described above in connection with the alkyl group.

The term "amino group" includes a nitrogen atom that is covalently bonded to at least one carbon atom or heteroatom. The amino group includes —NH$_2$ and substituted moieties. Also, examples of the amino group include an alkylamino group, in which a nitrogen atom is attached to at least one additional alkyl group, and an aryl amino group or a diarylamino group, in which a nitrogen atom is attached to at least one or two independently selected aryl groups.

An electrolyte of a lithium battery according to an example embodiment includes a non-aqueous organic solvent; a lithium salt; and, as described above, an additive including a triazine triphosphonate compound.

The additive for an electrolyte of a lithium battery includes the triazine triphosphonate compound. Without being bound by theory, it is believed that the triazine triphosphonate compound decomposes on the surfaces of the positive electrode and the negative electrode, thereby forming a stable solid electrolyte interface (SEI) layer on the surface of the positive electrode and the negative electrode. As a result, the stability of the lithium battery may be improved.

In an implementation, the additive may be the triazine triphosphonate compound. The additive, e.g., the triazine phosphonate compound, may be added to the electrolyte in an amount of, e.g., about 0.001 wt % to about 10 wt % based on the total weight of the electrolyte. The amount of the additive may be suitably varied. For example, an amount of the triazine phosphonate compound in the organic electrolytic solution may be in a range of about 0.01 wt % to about 5 wt % based on the total weight of the organic electrolytic solution. For example, the amount of the triazine triphosphonate compound may be in a range of about 0.1 wt % to about 1 wt % based on the total weight of the electrolyte. When the additive is added within the aforementioned range, the stability of a lithium secondary battery may be improved without a reduction in output power characteristics and lifetime characteristics.

The non-aqueous organic solvent serves as a medium via which ions for an electrochemical reaction of a battery transfer.

The non-aqueous organic solvent may include one or more of, e.g., a carbonate-based solvent, an ester-based solvent, an ether-based solvent, a ketone-based solvent, an alcohol-based solvent, or an aprotic solvent.

Examples of the carbonate-based solvent include dimethyl carbonate (DMC), diethyl carbonate (DEC), dipropyl carbonate (DPC), methyl propyl carbonate (MPC), ethyl propyl carbonate (EPC), methyl ethyl carbonate (MEC), ethylene carbonate (EC), propylene carbonate (PC), and butylene carbonate (BC). Examples of the ester-based solvent include methyl acetate, ethyl acetate, n-propyl acetate, dimethylacetate, methyl propionate, ethyl propionate, γ-butyrolactone, decanolide, valerolactone, mevalonolactone, and caprolactone.

Examples of the ether-based solvent include dibutyl ether, tetraglyme, diglyme, dimethoxyethane, 2-methyltetrahydrofuran, and tetrahydrofuran. For example, the ketone-based solvent may be cyclohexanone. The alcohol-based solvent may be, e.g., ethyl alcohol, isopropyl alcohol, or the like. Examples of the aprotic solvent include: nitriles such as R—CN where R is a linear, branched, or cyclic C2 to C20 hydrocarbon group and may have a double-bond aromatic ring or ether bond; amides such as dimethylformamide; dioxolanes such as 1,3-dioxolane; and sulfolanes.

The non-aqueous organic solvent may be used alone or in combination. When non-aqueous organic solvents are used in combination, a mixed ratio may be suitable adjusted with respect to the desired performance of the battery to be manufactured.

Also, a cyclic carbonate and a chain carbonate may be mixed to be used as the carbonate-based solvent. For example, the cyclic carbonate and the chain carbonate may be mixed at a volume ratio of about 1:1 to about 1:9, which may provide an electrolyte having excellent performance.

The non-aqueous organic solvent may further include an aromatic hydrocarbon-based organic solvent along with the carbonate-based solvent. For example, the carbonate-based solvent and the aromatic hydrocarbon-based organic solvent may be mixed at a volume ratio of about 1:1 to about 30:1.

The aromatic hydrocarbon-based compound represented by Formula 4 below may be used as the aromatic hydrocarbon-based organic solvent,

[Formula 4]

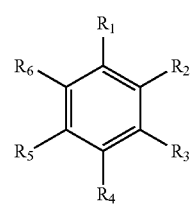

According to an example embodiment, in Formula 4, $R_1$ to $R_6$ are each independently hydrogen, a halogen group, an alkyl group of $C_1$ to $C_{10}$, a haloalkyl group of $C_1$ to $C_{10}$ or a combination thereof.

Examples of the aromatic hydrocarbon-based organic solvent include benzene, fluoro benzene, 1,2-difluoro benzene, 1,3-difluoro benzene, 1,4-difluoro benzene, 1,2,3-trifluoro benzene, 1,2,4-trifluoro benzene, chloro benzene, 1,2-dichloro benzene, 1,3-dichloro benzene, 1,4-dichloro benzene, 1,2,3-trichloro benzene, 1,2,4-trichloro benzene, iodo benzene, 1,2-diiodo benzene, 1,3-diiodo benzene, 1,4-diiodo benzene, 1,2,3-triiodo benzene, 1,2,4-triiodo benzene, toluene, fluoro toluene, 1,2-difluoro toluene, 1,3-difluoro toluene, 1,4-difluoro toluene, 1,2,3-trifluoro toluene, 1,2,4-trifluoro toluene, chloro toluene, 1,2-dichloro toluene, 1,3-dichloro toluene, 1,4-dichloro toluene, 1,2,3-trichloro toluene, 1,2,4-trichloro toluene, iodo toluene, 1,2-diiodo toluene, 1,3-diiodo toluene, 1,4-diiodo toluene, 1,2,3-triiodo toluene, 1,2,4-triiodo toluene, xylene, a combination thereof, etc.

The non-aqueous electrolyte may further include a vinylene carbonate-based or an ethylene carbonate-based compound represented by Formula 5 below, which may improve the longevity of a battery,

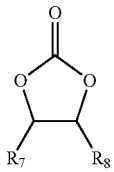

[Formula 5]

According to an example embodiment, in Formula 5, $R_7$ and $R_8$ are each independently hydrogen, a halogen group, a cyano group (CN), a nitro group ($NO_2$), or a $C_1$-$C_5$ fluoro alkyl group. In an implementation, at least one selected from $R_7$ and $R_8$ is a halogen group, a cyano group (CN), a nitro group ($NO_2$), or a $C_1$-$C_5$ fluoro alkyl group.

Examples of an ethylene carbonate-based compound include difluoro ethylene carbonate, chloroethylene carbonate, dichloroethylene carbonate, bromoethylene carbonate, di bromoethylene carbonate, nitroethylene carbonate, cyanoethylene carbonate, and fluoroethylene carbonate. When the vinylene carbonate-based or the ethylene carbonate-based compound is further used, the lifetime of a battery may be improved by adjusting the added amount.

The lithium salt is dissolved in the non-aqueous organic solvent, and supplies lithium ions in a battery to operate a lithium secondary battery while facilitating the migration of ions between a positive electrode and a negative electrode. Examples of the lithium salt include $LiPF_6$, $LiBF_4$, $LiSbF_6$, $LiAsF_6$, $LiC_4F_9SO_3$, $LiClO_4$, $LiAlO_2$, $LiAlCl_4$, $LiN(C_xF_{2x+1}SO_2)(C_yF_{2y+1}SO_2)$ where x and y are each independently an integer of 1 to 10, LiCl, LiI, $LiB(C_2O_4)_2$ (lithium bis (oxalato)borate; LiBOB) or a combination thereof. A supporting electrolyte salt includes the aforementioned examples. The concentration of the lithium salt may be in a range of about 0.01 M to about 2.0 M When the lithium salt is used within the range, an electrolyte may have a proper conductivity and viscosity to have an excellent performance, thereby facilitating the effective migration of lithium ions.

According to an example embodiment, the non-aqueous organic solvent may include one or more of dimethyl carbonate (DMC), diethyl carbonate (DEC), dipropyl carbonate (DPC), methyl propyl carbonate (MPC), ethyl propyl carbonate (EPC), methyl ethyl carbonate (MEC), ethylene carbonate (EC), propylene carbonate (PC), butylene carbonate (BC), fluoroethylene carbonate (FEC), vinylene carbonate (VC), acetonitrile, succinonitrile (SN), dimethyl sulfoxide, dimethyl formamide, dimethyl acetamide, γ-butyrolactone, or tetrahydrofuran.

According to an example embodiment, the non-aqueous organic solvent may include a mixed solvent of ethylene carbonate (EC) and ethyl methyl carbonate (EMC), or a mixed solvent of ethylene carbonate (EC), ethyl methyl carbonate (EMC), and diethylene carbonate (DEC).

The electrolyte for a lithium battery may further include another additive in order to further improve cycle characteristics by facilitating the forming of a stable SEI layer or film on the surface of an electrode.

Examples of the other additive include tris(trimethylsilyl) phosphate (TMSPa); lithium difluoro(oxalato)borate (LiFOB); vinylene carbonate (VC); propane sultone (PS); succinonitrile (SN); $LiBF_4$; a silane compound having a functional group, which may form a siloxane bond, such as an acrylic group, an amino group, epoxy, methoxy, ethoxy, and vinyl; and a silazane compound such as hexamethyldisilazane. The other additive may be added alone or in a combination of two or more.

A lithium battery according to another embodiment includes a positive electrode, a negative electrode, and an electrolyte for a lithium battery that is disposed between the positive electrode and the negative electrode. The lithium battery may be of various types, and may be a lithium primary battery or a lithium secondary battery such as a lithium ion battery, a lithium ion polymer battery, or a lithium sulfur battery. The lithium battery may be manufactured by a suitable method.

The positive electrode may include a positive electrode current collector and a positive active material layer formed on the positive electrode current collector.

The positive electrode current collector may be prepared with a thickness of, e.g., about 3 μm to about 500 μm. A suitable current collector that does not cause a chemical change in a battery and has a high conductivity may be used as the positive electrode current collector. For example, copper, stainless steel, aluminum, nickel, titanium, calcined carbon, or copper or stainless steel of which a surface is treated with carbon, nickel, titanium, or silver, aluminum-cadmium alloy, and the like may be used. Also, the positive electrode current collector may form fine bumps on a surface thereof to increase an adhesive strength of the positive active material and may be used in various forms, such as a film, a sheet, a foil, a net, a porous structure, a foam structure, or a non-woven structure.

The positive active material layer may include a positive active material and a binder. The positive active material layer may include a conducting agent.

A suitable positive active material may be used. For example, the positive active material may be a compound represented by at least one selected from $Li_aA_{1-b}B_bD_2$ (where, $0.90 \leq a \leq 1$ and $0 \leq b \leq 0.5$); $Li_aE_{1-b}B_bO_{2-c}D_c$ (where, $0.90 \leq a \leq 1$, $0 \leq b \leq 0.5$, and $0 \leq c \leq 0.05$); $LiE_{2-b}B_bO_{4-c}D_c$ (where, $0 \leq b \leq 0.5$ and $0 \leq c \leq 0.05$); $Li_aNi_{1-b-c}Co_bB_cD_\alpha$ (where, $0.90 \leq a \leq 1$, $0 \leq b \leq 0.5$, $0 \leq c \leq 0.05$, and $0 \leq \alpha \leq 2$); $Li_aNi_{1-b-c}Co_bB_cO_{2-\alpha}F_\alpha$ (where, $0.90 \leq a \leq 1$, $0 \leq b \leq 0.5$, $0 \leq c \leq 0.05$, and $0 < \alpha < 2$); $Li_aNi_{1-b-c}Co_bB_cO_{2-\alpha}F_2$ (where, $0.90 \leq a \leq 1$, $0 \leq b \leq 0.5$, $0 \leq c \leq 0.05$, and $0 \leq \alpha \leq 2$); $Li_aNi_{1-b-c}Mn_bB_cD_\alpha$ (where, $0.90 \leq a \leq 1$, $0 \leq b \leq 0.5$, $0 \leq c \leq 0.05$, and $0 < \alpha \leq 2$); $Li_aNi_{1-b-c}Mn_bB_cO_{2-\alpha}F_\alpha$ (where, $0.90 \leq a \leq 1$, $0 \leq b \leq 0.5$, $0 \leq c \leq 0.05$, and $0<\alpha<2$); $Li_aNi_{1-b-c}Mn_bB_cO_{2-\alpha}F_2$ (where, $0.90\le a\le1$, $0\le b\le0.5$, $0\le c\le0.05$, and $0<\alpha<2$); $Li_aNi_bE_cG_dO_2$ (where, $0.90\le a\le1$, $0\le b\le0.9$, $0\le c\le0.5$, and $0.001<d<0.1$); $Li_aNi_{b-}Co_cMn_dGeO_2$ (where, $0.90\le a\le1$, $0\le b\le0.9$, $0\le c\le0.5$, $0\le d\le0.5$, and $0.001\le e\le0.1$); $Li_1NiG_bO_2$ (where, $0.90\le a\le1$ and $0.001\le b\le0.1$); $Li_aCoG_bO_2$ (where, $0.90\le a\le1$ and $0.001\le b\le0.1$); $Li_aMnG_bO_2$ (where, $0.90\le a\le1$ and $0.001\le b\le0.1$); $Li_aMn_2G_bO_4$ (where, $0.90\le a\le1$ and $0.001\le b\le0.1$); $QO_2$; $QS_2$; $LiQS_2$; $V_2O_5$; $LiV_2O_5$; $LiIO_2$; $LiNiVO_4$; $Li_{(3-f)}J_2(PO_4)_3$ (where, $0\le f\le2$); $Li_{(3-f)}Fe_2(PO_4)_3$ (where, $0\le f\le2$); and $LiFePO_4$.

In the formulae above, A is Ni, Co, Mn, or a combination thereof; B is Al, Ni, Co, Mn, Cr, Fe, Mg, Sr, V, a rare earth element, or a combination thereof; D is O, F, S, P, or a combination thereof; E is Co, Mn, or a combination thereof; F is F, S, P, or a combination thereof; G is Al, Cr, Mn, Fe, Mg, La, Ce, Sr, V, or a combination thereof; Q is Ti, Mo, Mn, or a combination thereof; I is Cr, V, Fe, Sc, Y, or a combination thereof; and J is V, Cr, Mn, Co, Ni, Cu, or a combination thereof.

For example, the positive active material may include one or more composite oxides of lithium and a metal selected from the group consisting of cobalt, manganese, nickel, and combinations thereof. For example, the positive active material may be a compound represented by any one of the Formulae: $LiCoO_2$, $LiMn_xO_{2x}$ where x=1, 2, $LiNi_{1-x}Mn_xO_{2x}$ where $0<x<1$, $LiNi_{1-x-y}Co_xMn_yO_2$ where $0\le x\le0.5$, $0\le y\le0.5$, and $FePO_4$.

The compound may have a coating layer on a surface thereof, or the compound may be mixed with a compound having a coating layer. The coating layer may include a coating element compound of an oxide or a hydroxide of a coating element, an oxyhydroxide of a coating element, an oxycarbonate of a coating element, or a hydroxycarbonate of a coating element. The compound forming the coating layer may be amorphous or crystalline. A coating element included in the coating layer may be Mg, Al, Co, K, Na, Ca, Si, Ti, V, Sn, Ge, Ga, B, As, Zr, or a mixture thereof. A process of forming the coating layer may be carried out by adding the elements into the compound by using a suitable method (e.g., spray-coating or dipping) that does not negatively affect the properties of the positive active material.

The binder may attach positive active material particles to one another and attach the positive active material to a current collector. Examples of the binder include polyvinyl alcohol, carboxymethylcellulose, hydroxypropyl cellulose, diacetyl cellulose, polyvinylchloride, carboxylated polyvinylchloride, polyvinyl fluoride, a polymer including ethylene oxide, polyvinylpyrrolidone, polyurethane, polytetrafluoroethylene, polyvinylidene fluoride, polyethylene, polypropylene, styrene-butadiene rubber, acrylated styrene-butadiene rubber, epoxy resin, nylon, etc.

The conducting agent may be used for an electrode to have enhanced conductivity. A suitable conducting agent that does not cause a chemical change in a battery may be used. Examples of an electron conducting agent include natural graphite, artificial graphite, carbon black, acetylene black, ketjen black, carbon fiber, and metal powder or metal fiber made of copper, nickel, aluminum, silver or the like. Also, a conductive material such as a polyphenylene derivative may be used alone or in a combination of one or more conductive materials.

The negative electrode may include a negative electrode current collector and a negative active material layer formed on the negative electrode current collector.

The negative electrode current collector may be prepared with a thickness of, e.g., about 3 μm to about 500 μm. A suitable current collector that does not cause a chemical change in a battery and has a high conductivity may be used as the negative electrode current collector. For example, copper, stainless steel, aluminum, nickel, titanium, calcined carbon, copper or stainless steel of which a surface is treated with carbon, nickel, titanium, or silver, aluminum-cadmium alloy and the like may be used. Also, the negative electrode current collector may form fine bumps on a surface thereof to increase an adhesive strength of the negative active material and may be used in various forms, such as a film, a sheet, a foil, a net, a porous structure, a foam structure, or a non-woven structure.

The negative active material layer may include a negative active material and a binder. The negative active material layer may include a conducting agent.

A suitable negative active material may be used.

Examples of the negative active material include a lithium metal, a metal alloyable with lithium, a transition metal oxide, a material capable of doping and dedoping lithium, a material capable of reversibly intercalating and deintercalating lithium ions, and a combination of two or more thereof may also be used.

Examples of the metal that is alloyable with lithium include sodium (Na), potassium (K), rubidium (Rb), cesium (Cs), francium (Fr), beryllium (Be), magnesium (Mg), calcium (Ca), strontium (Sr), silicon (Si), antimoy (Sb), lead (Pb), indium (In), zinc (Zn), barium (Ba), radium (Ra), germanum (Ge), aluminum (Al), and tin (Sn).

Examples of the transition metal oxide include tungsten oxide, molybdenum oxide, titanium oxide, lithium titanium oxide, vanadium oxide, and lithium vanadium oxide.

Examples of the material capable of doping and dedoping lithium include Si, Sn, Al, Ge, Pb, Bi, Sb, $SiO_x$ ($0<x<2$), Si—Y alloy (wherein Y is an alkali metal, an alkali earth metal, a Group XI element, a Group XII element, a Group XIII element, a Group XIV element, a Group XV element, a Group XVI element, a transition metal, a rare earth element, or a combination thereof and is not Si), $SnO_x$ ($0<x<2$), an Sn—Y alloy (wherein Y is an alkali metal, an alkali earth metal, a Group XI element, a Group XII element, a Group XIII element, a Group XIV element, a Group XV element, a Group XVI element, a transition metal, a rare earth element, or a combination thereof and is not Sn). The element Y may be Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir Pd, Pt, Cu, Ag, Au, Zn, Cd, B, Al, Ga, Sn, In, Ti, Ge, P, As, Sb, Bi, S, Se, Te, Po, or a combination thereof.

A suitable carbon-based negative active material may be used for a lithium battery as the material capable of reversibly intercalating and deintercalating lithium ions. For example, the carbon-based negative active material may be a crystalline carbon, an amorphous carbon, or a combination thereof. Examples of the crystalline carbon include natural graphite, artificial graphite, expandable graphite, graphene, fullerene soot, carbon nanotubes, and carbon fiber. Examples of the amorphous carbon include soft carbon (low-temperature calcined carbon) or hard carbon, mesophase pitch carbide, and calcined coke. The carbon-based negative active material may be used in a shape such as a sphere shape, a plate shape, a fiber shape, a tube shape, or a power shape.

The binder may attach negative active material particles to one another and attach the negative active material to a current collector. Examples of the binder include polyvinyl alcohol, carboxymethylcellulose, hydroxypropyl cellulose, polyvinylchloride, carboxylated polyvinylchloride, polyvinyl fluoride, a polymer including ethylene oxide, polyvinylpyrrolidone, polyurethane, polytetrafluoroethylene, polyvinylidene fluoride, polyethylene, polypropylene, styrene-butadiene rubber, acrylated styrene-butadiene rubber, epoxy resin, nylon, etc.

The conducting agent may be used for an electrode to have enhanced conductivity. A suitable conducting agent that that does not cause a chemical change in a battery may be used. Examples of the conducting agent include a carbon-based material such as natural graphite, artificial graphite, carbon black, acetylene black, ketjen black, and carbon fiber; a metal-based material including a metal powder or fiber made of copper, nickel, aluminum, silver or the like; a conductive polymer such as a polyphenylene derivative; or a combination thereof.

The positive electrode and the negative electrode may be prepared by mixing the active material, the conducting agent and the binder with the solvent to obtain an active material composition, and then by coating each current collector with the active material composition.

The solvent may include, for example, N-methylpyrrolidone (NMP), acetone, water, etc.

The positive electrode and the negative electrode may be separated from each other by a separator, and a suitable separator for a lithium battery may be used. For example, a material that has low resistance to ion migration of an electrolyte and has an excellent electrolytic solution retaining capability is suitable for forming the separator. For example, a material for forming the separator may be selected from glass fiber, polyester, Teflon, polyethylene, polypropylene, polytetrafluoroethylene (PTFE), and a combination thereof, and each of them may be in a non-woven fabric or woven fabric form. Pores included in the separator may have a diameter in a range of about 0.01 μm to about 10 μm, and the separator may have a thickness in a range of about 5 μm to about 300 μm.

The separator may be a single layer or a multi-layer. Examples of the olefin-based polymer include polyethylene, polypropylene, polyvinylidene fluoride or a multi-layer including two or more layers thereof, and a mixed multi-layer, such as a 2-layer separator of polyethylene/polypropylene, a 3-layer separator of polyethylene/polypropylene/polyethylene, or a 3-layer separator of polypropylene/polyethylene/polypropylene.

When a solid electrolyte such as a polymer is used as an electrolyte, the solid electrolyte may serve as a separating layer.

FIG. 1 shows a typical structure of a lithium battery 30 according to an example embodiment.

Referring to FIG. 1, the lithium battery 30 includes a positive electrode 23, a negative electrode 22, and a separator 24 disposed between the positive electrode 23 and the negative electrode 22. The positive electrode 23, the negative electrode 22, and the separator 24 are wound or bent to be accommodated in a battery case 25. Then, an electrolyte is loaded into the battery case 25 and sealed with an encapsulating member 26 to prepare the lithium battery 30. The battery case 25 may be formed in a shape such as a cylinder shape, a rectangular shape, or a thin film shape. For example, the lithium battery may be a large thin film type battery or may be a lithium ion battery. The separator may be disposed between the positive electrode and the negative electrode to form a battery assembly.

Battery assemblies may be stacked in a bi-cell structure and impregnated with an organic electrolytic solution, and the resultant structure may be accommodated in a pouch and sealed, thereby completing the manufacture of a lithium ion polymer battery.

In addition, the battery assemblies may be stacked on each other to form a battery pack, and the battery pack may be used in high capacity and high-performance devices, such as a notebook computer, a smartphone, an electric vehicle, and the like.

Since the lithium battery has long longevity and high-rate characteristics, the lithium battery is suitable for use in an electric vehicle (EV). For example, the lithium battery may be used in a hybrid vehicle such as a plug-in hybrid electric vehicle (PHEV). The lithium battery may be used in fields that require a high output power, a high voltage, and operation at a high temperature, such as an electric bicycle, an electric tool, and so forth.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Preparation of an Electrolyte

Preparation Example 1

Ethylene carbonate (EC), ethyl methyl carbonate (EMC), and dimethyl carbonate (DMC), which are non-aqueous organic solvents, were mixed at a volume ratio of 30:50:20 to obtain a mixed solvent, and then $LiPF_6$ was added thereto until the concentration of $LiPF_6$ reached 0.9 M. The additive represented by Formula 3 was added thereto in an amount of 0.5 wt % based on 100 wt % of a total weight of an electrolyte, and then dissolved to prepare the electrolyte.

Preparation Example 2

An electrolyte was prepared in the same manner as in Preparation Example 1, except that the added amount of the compound of Formula 3 was changed to 1 wt % instead of 0.5 wt %.

Preparation Example 3

An electrolyte was prepared in the same manner as in Preparation Example 1, except that the added amount of the compound of Formula 3 was changed to 2 wt % instead of 0.5 wt %.

Comparative Preparation Example 1

$LiPF_6$ was added to a mixed solvent, in which EC, DMC, and DEC were mixed at a volume ratio of 30:50:20, until the concentration of the solvent reached 0.9 M to prepare an electrolyte without adding the compound represented by Formula 3 thereto.

Preparation of Lithium Battery

Example 1

A positive active material powder, which is $LiCoO_2$, and a carbon conducting agent (Super-P manufactured by Timcal Ltd.) were mixed evenly in a weight ratio of 90:5, and then a polyvinylidene fluoride (PVDF) binder solution was added thereto to prepare a positive active material slurry in which a weight ratio of active material:carbon conducting agent: binder was 90:5:5. After coating an aluminum foil having a thickness of 15 μm with the positive active material slurry, the aluminum foil was dried and pressed to prepare a positive electrode.

Also, graphite (MC20) and a PVDF binder were mixed in a weight ratio of 1:1, and then N-methylpyrrolidone was added thereto in a solid amount of 60 wt % in order to adjust a viscosity. As a result, a negative active material slurry was prepared. After coating a copper foil having a thickness of 15 μm with the negative active material slurry, the copper foil was dried and pressed to prepare a negative electrode.

An 18650-type full cell was prepared by using the positive electrode and the negative electrode prepared in the above processes, and a 20 μm thickness separator (STAR20 manufactured by Asahi) made of polyethylene, and by loading an electrolyte thereto. Here, the electrolyte in Preparation Example 1 was used.

Example 2

A full cell was prepared in the same manner as in Example 1, except that the electrolyte in Preparation Example 2 was used instead of the electrolyte in Preparation Example 1.

Example 3

A full cell was prepared in the same manner as in Example 1, except that the electrolyte in Preparation Example 3 was used instead of the electrolyte in Preparation Example 1.

Comparative Example 1

A full cell was prepared in the same manner as in Example 1, except that the electrolyte in Comparative Preparation Example 1 was used instead of the electrolyte in Preparation Example 1.

Evaluation Example 1: Evaluation Charge/Discharge Characteristics at a High Temperature of 45° C.

The lithium batteries prepared according to Examples 1 to 3 and Comparative Example 1 were charged at a constant current at a 0.1 C rate at 25° C. until the voltages of the lithium batteries reached 4.4 V (vs. Li). Then, in a constant voltage mode of 4.4 V (vs. Li), the lithium battery was cut-off at a 0.05 C rate. Next, the lithium batteries were discharged at a constant current at a 0.1 C rate until the voltages of the lithium batteries reached 2.75 V (vs. Li). (formation step, $1^{st}$ cycle).

The lithium battery formed according to the $1^{st}$ cycle of the formation step was charged at a constant current at a 0.2 C rate at 25° C. until the voltage of the lithium battery reached 4.4 V (vs. Li). Then, in a constant voltage mode of 4.4 V (vs. Li), the lithium battery was cut-off at a 0.05 C rate. Next, the lithium batteries were discharged at a constant current at a 0.2 C rate until the voltages of the lithium batteries reached 2.75 V (vs. Li). (formation step, $2^{nd}$ cycle).

The lithium battery formed according to the $2^{nd}$ cycle of the formation step was charged at a constant current at a 1.0 C rate at 45° C. until the voltage of the lithium battery reached 4.4 V (vs. Li). Then, in a constant voltage mode of 4.4 V (vs. Li), the lithium battery was cut-off at a 0.05 C rate. Next, the lithium batteries were discharged at a constant current at a 1.0 C rate until the voltages of the lithium batteries reached 2.75 V (vs. Li). The charging and discharging cycle of the lithium battery was repeated 100 times.

There was a 10-minute time lapse between each charging and discharging cycle.

Figure 2:
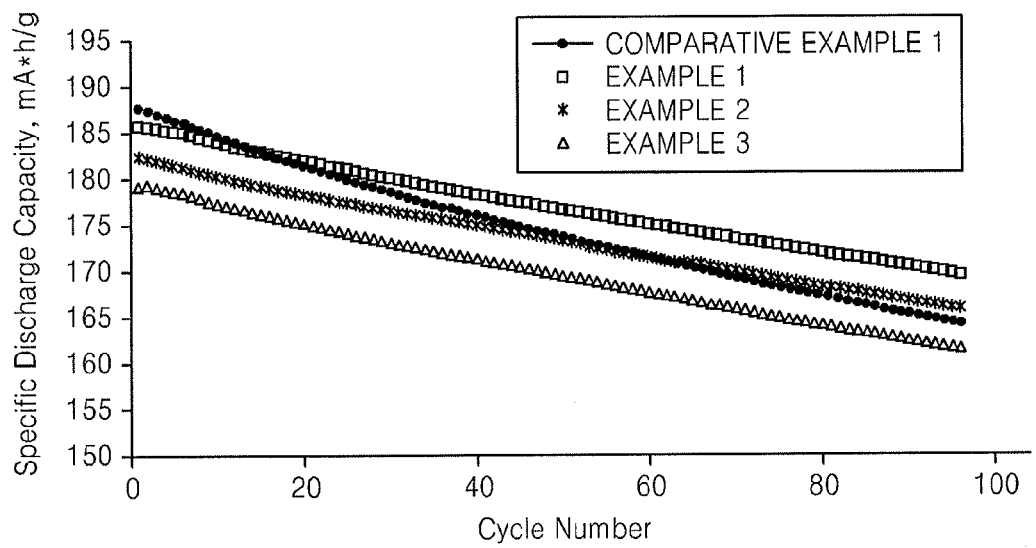
FIG. 2 illustrates a graph showing a specific discharge capacity for each cycle of lithium batteries manufactured in Examples 1 to 3 and Comparative Example 1.
Figure 3:
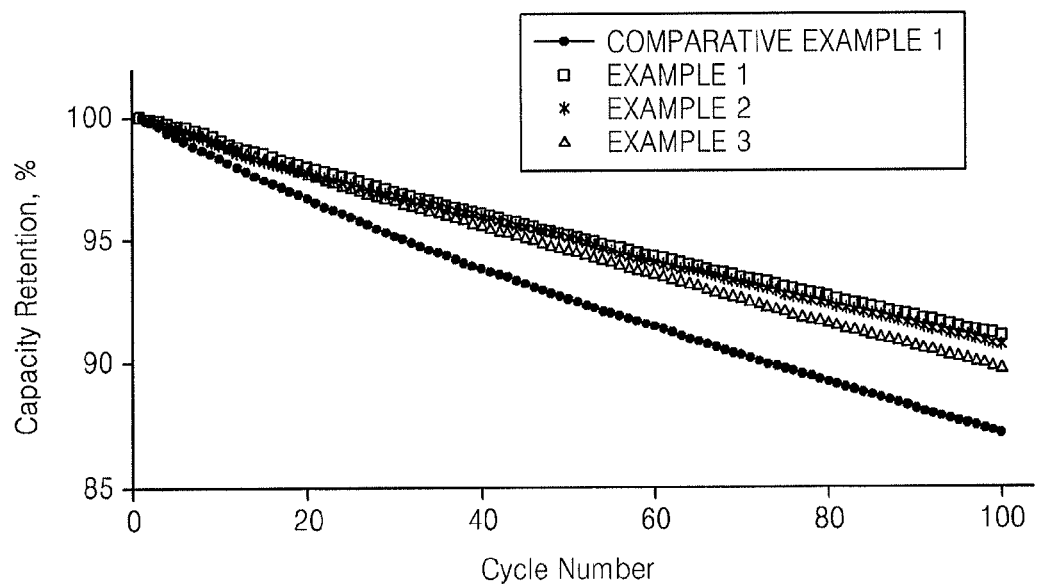
FIG. 3 illustrates a graph showing a capacity retention for each cycle of the lithium batteries manufactured in Examples 1 to 3 and Comparative Example 1.

FIG. 2 shows a discharge capacity for each cycle of each lithium battery prepared according to Examples 1 to 3 and Comparative Example 1, and FIG. 3 shows a capacity retention rate for each cycle of each lithium battery prepared according to Examples 1 to 3 and Comparative Example 1.

Here, capacity retention ratio (CRR) is defined by Equation 1 below.

$$\text{CRR}[\%]=[\text{discharge capacity for each cycle/discharge capacity for the } 1^{st} \text{ cycle}] \times 100 \qquad <\text{Equation 1}>$$

As shown in FIG. 2, the lithium batteries prepared according to Examples 1 to 3 showed smaller decreases in discharge capacity than that of the lithium battery prepared according to Comparative Example 1 as the cycle repeated.

Also, as shown in FIG. 3, the lithium batteries prepared according to Examples 1 to 3 had significantly improved lifetime characteristics at a high temperature, compared to that of lithium battery prepared according to Comparative Example 1.

Figure 4:
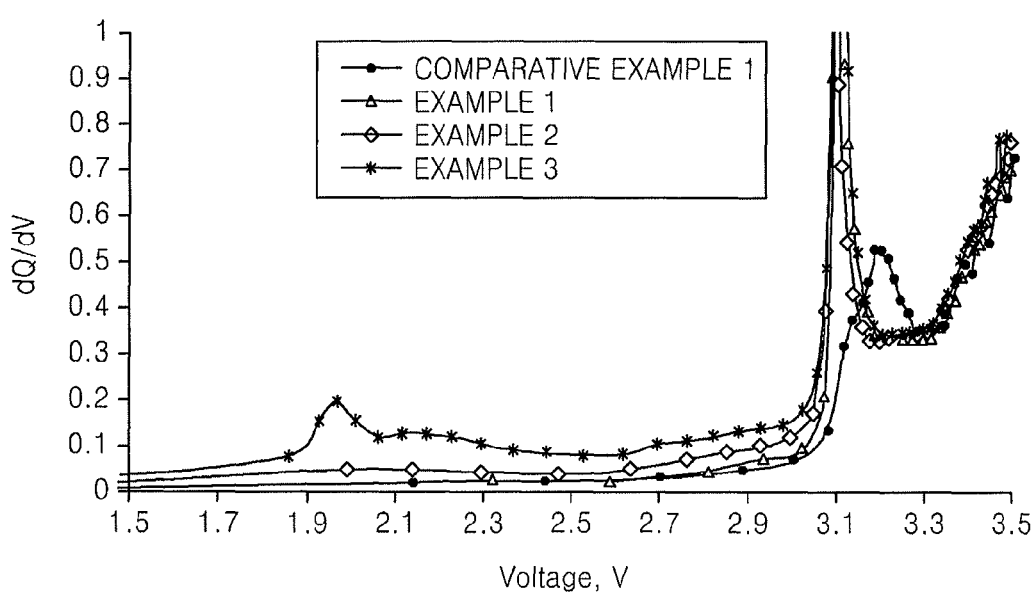
FIG. 4 illustrates a differential capacity (dQ/dV) curve for the first cycle of the lithium batteries manufactured in Examples 1 to 3 and Comparative Example 1.

Differential capacity (dQ/dV) curves for the first cycle of the lithium batteries prepared according to Examples 1 to 3 and Comparative Example 1 are shown in FIG. 4.

As shown in FIG. 4, lithium batteries of Examples 1 to 3 had a wide oxidation-reduction peak in a range of about 2.0 V to about 2.2 V, and a significant oxidation-reduction peak at about 3.1 V. On the other hand, lithium batteries of Comparative Example 1 had an oxidation-reduction peak at about 3.2 V. Without being bound by theory, it is believed that the triazine triphosphonate compound represented Formula 3, which was added to the lithium batteries of Examples 1-3, was decomposed earlier than a comparative non-aqueous organic solvent during the initial charging of the formation step, and then the compound formed a stable SEI layer on the surface of the negative electrode.

By way of summation and review, a lithium battery operates at a high voltage such that an aqueous electrolytic solution that has high reactivity to lithium may not be used. Therefore, an organic electrolytic solution may be used in the lithium battery. The organic electrolytic solution may be prepared by dissolving a lithium salt in an organic solvent. An organic solvent that is stable at a high voltage and has a high ion conductivity, a high permittivity and a low viscosity is suitable for the lithium battery.

When a carbonate-based polar non-aqueous solvent is used in a lithium battery, a side reaction between a negative electrode/positive electrode and an electrolytic solution occurs at an initial charging, and an irreversible reaction may occur when the lithium battery is excessively charged.

Due to the irreversible reaction, a passivation layer such as a solid electrolyte interface layer (SEI layer) is formed on the surface of the negative electrode. The SEI layer prevents an electrolytic solution from being decomposed during charging and discharging, and serves as an ion tunnel. The higher stability and the lower resistance the SEI layer has, the more improved lifetime characteristics the lithium battery has.

Also, a protection layer is formed on the surface of the positive electrode due to the irreversible reaction. The protection layer prevents an electrolytic solution from being decomposed during charging and discharging and serves as an ion tunnel. The higher stability the protection layer has at a high temperature, the more improved lifetime characteristics the lithium battery may have.

Various additives may be considered in order to stabilize the SEI layer and/or the protection layer. However, the SEI layer formed by using an additive may deteriorate at a high temperature. Thus, the stability of the SEI layer and/or the protection layer may degrade at a high temperature. An electrolyte forming the SEI layer and/or the protection layer, which have the improved stability at a high temperature, is desired.

As described above, according to the one or more of the above embodiments, the lifetime characteristics of a lithium battery at a high temperature may be improved in a lithium battery that includes an additive for an electrolyte of a lithium battery according to an example embodiment in the electrolyte.

As described above, embodiments may provide an additive for an electrolyte of a lithium battery that may improve the lifetime characteristics of the lithium battery at a high temperature.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A lithium battery electrolyte, comprising:
   a non-aqueous organic solvent;
   a lithium salt; and
   an additive, the additive including a triazine triphosphonate compound.

2. The electrolyte as claimed in claim 1, wherein the triazine triphosphonate compound is a 1,3,5-triazine-2,4,6-triphosphonate compound.

3. The electrolyte as claimed in claim 1, wherein the triazine triphosphonate compound is represented by Formula 1 below:

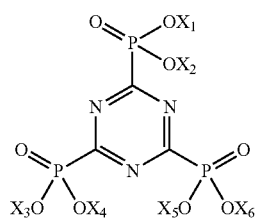

[Formula 1]

wherein:
$X_1$, $X_2$, $X_3$, $X_4$, $X_5$, and $X_6$ are each independently hydrogen, a halogen atom, a substituted or unsubstituted $C_1$-$C_{30}$ alkyl group, a substituted or unsubstituted $C_1$-$C_{30}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_7$-$C_{20}$ arylalkyl group, a substituted or unsubstituted $C_2$-$C_{20}$ heteroaryl group, a substituted or unsubstituted $C_2$-$C_{20}$ heteroaryloxy group, a substituted or unsubstituted $C_2$-$C_{20}$ heteroarylalkyl group, a substituted or unsubstituted $C_4$-$C_{20}$ cyclic group, a substituted or unsubstituted $C_4$-$C_{20}$ cyclic alkyl group, a substituted or unsubstituted $C_2$-$C_{20}$ heterocyclic group, a substituted or unsubstituted $C_2$-$C_{20}$ heterocyclic alkyl group, a cyano group, an amino group, an amidino group, a hydrazine group, a hydrazone group, a nitro group, a phosphonate group, a silyl group, a carboxyl group or a salt thereof, a sulfonyl group, a sulfamoyl group, a sulfonic acid group or a salt thereof, or a phosphoric acid group or a salt thereof.

4. The electrolyte as claimed in claim 1, wherein the triazine triphosphonate compound is a silylated triazine triphosphonate compound.

5. The electrolyte as claimed in claim 1, wherein the triazine triphosphonate compound is a silylated 1,3,5-triazine-2,4,6-triphosphonate compound.

6. The electrolyte as claimed in claim 1, wherein the triazine triphosphonate compound is represented by Formula 2 below:

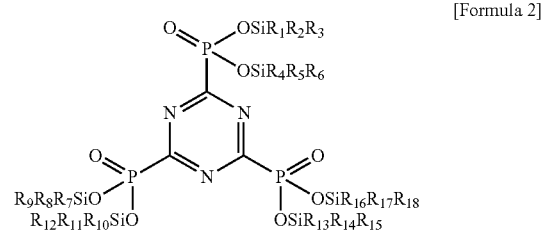

[Formula 2]

wherein:
$R_1$ to $R_{18}$ are each independently hydrogen, a halogen atom, a substituted or unsubstituted $C_1$-$C_{30}$ alkyl group, a substituted or unsubstituted $C_1$-$C_{30}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_7$-$C_{20}$ arylalkyl group, a substituted or unsubstituted $C_2$-$C_{20}$ heteroaryl group, a substituted or unsubstituted $C_2$-$C_{20}$ heteroaryloxy group, a substituted or unsubstituted $C_2$-$C_{20}$ heteroarylalkyl group, a substituted or unsubstituted $C_4$-$C_{20}$ cyclic group, a substituted or unsubstituted $C_4$-$C_{20}$ cyclic alkyl group, a substituted or unsubstituted $C_2$-$C_{20}$ heterocyclic group, a substituted or unsubstituted $C_2$-$C_{20}$ heterocyclic alkyl group, a cyano group, a hydroxyl group, an amino group, an amidino group, a hydrazine group, a hydrazone group, a nitro group, a thiol group, a carboxyl group or a salt thereof, a sulfonyl group, a sulfamoyl group, a sulfonic acid group or a salt thereof, or a phosphoric acid group or a salt thereof.

7. The electrolyte as claimed in claim 6, wherein, in Formula 2, $R_1$ to $R_{18}$ are each independently substituted or unsubstituted $C_1$-$C_{30}$ alkyl groups.

8. The electrolyte as claimed in claim 6, wherein, in Formula 2, $R_1$ to $R_{18}$ are each independently a methyl group, an ethyl group, a propyl group, an isopropyl group, a butyl group, a tert-butyl group, a trifluoromethyl group, or a tetrafluoroethyl group.

9. The electrolyte as claimed in claim 1, wherein the triazine triphosphonate compound is represented by Formula 3 below:

[Formula 3]

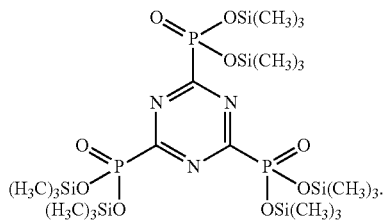

10. The electrolyte as claimed in claim 1, wherein the amount of the additive is in a range of about 0.001 wt % to about 10 wt % based on the total weight of the electrolyte.

11. The electrolyte as claimed in claim 1, wherein the amount of the additive is in a range of about 0.01 wt % to about 5 wt % based on the total weight of the electrolyte.

12. The electrolyte as claimed in claim 1, wherein the non-aqueous organic solvent includes one or more of a carbonate-based solvent, an ester-based solvent, an ether-based solvent, a ketone-based solvent, an alcohol-based solvent, or an aprotic solvent.

13. The electrolyte as claimed in claim 1, wherein the non-aqueous organic solvent includes one or more of dimethyl carbonate (DMC), diethyl carbonate (DEC), dipropyl carbonate (DPC), methyl propyl carbonate (MPC), ethyl propyl carbonate (EPC), methyl ethyl carbonate (MEC), ethylene carbonate (EC), propylene carbonate (PC), butylene carbonate (BC), fluoroethylene carbonate (FEC), vinylene carbonate (VC), acetonitrile, succinonitrile (SN), dimethyl sulfoxide, dimethyl formamide, dimethyl acetamide, γ-butyrolactone, tetrahydrofuran, or ethyl propionate (EP).

14. The electrolyte as claimed in claim 1, wherein the lithium salt includes one or more of $LiPF_6$, $LiBF_4$, $LiSbF_6$, $LiAsF_6$, $LiC4F_9SO_3$, $LiClO_4$, $LiALO_2$, $LiAlCl_4$, $LiN(C_xF_{2x+1}SO_2)(C_yF_{2y+1}SO_2)$ where x and y are each independently an integer of 1 to 10, LiCl, LiI, $LiB(C_2O_4)_2$(lithium bis(oxalato)borate), or a combination thereof.

15. The electrolyte as claimed in claim 1, wherein the concentration of the lithium salt is in a range of about 0.1 M to about 2.0 M.

16. A lithium battery, comprising:
a positive electrode;
a negative electrode; and
the electrolyte as claimed in claim 1.

* * * * *